United States Patent
Gahlert

(10) Patent No.: US 10,271,927 B2
(45) Date of Patent: Apr. 30, 2019

(54) CERAMIC DENTAL IMPLANT

(75) Inventor: Michael Gahlert, Munich (DE)

(73) Assignee: STRAUMANN HOLDING AG, Basel (CH)

( * ) Notice: Subject to any disclaimer, the term of this patent is extended or adjusted under 35 U.S.C. 154(b) by 542 days.

(21) Appl. No.: 13/228,642

(22) Filed: Sep. 9, 2011

(65) Prior Publication Data

US 2011/0318708 A1 Dec. 29, 2011

Related U.S. Application Data

(62) Division of application No. 10/496,814, filed as application No. PCT/EP02/13187 on Nov. 23, 2002.

(30) Foreign Application Priority Data

Nov. 30, 2001 (DE) .................................. 101 59 683

(51) Int. Cl.
*A61C 8/00* (2006.01)

(52) U.S. Cl.
CPC .......... *A61C 8/0015* (2013.01); *A61C 8/0012* (2013.01); *A61C 8/0013* (2013.01); *A61C 8/0022* (2013.01); *A61C 8/0066* (2013.01); *A61C 8/0069* (2013.01); *A61C 8/0075* (2013.01); *A61C 8/0089* (2013.01); *A61C 2008/0046* (2013.01)

(58) Field of Classification Search
CPC ....... A61C 8/00; A61C 8/0015; A61C 8/0012; A61C 8/0013; A61C 8/0022; A61C 8/0066; A61C 8/0069; A61C 8/0075; A61C 8/0089

USPC ...................... 433/172–176, 201.1; 501/103; 606/300–330
See application file for complete search history.

(56) References Cited

U.S. PATENT DOCUMENTS

| | | | |
|---|---|---|---|
| 4,145,764 A | 5/1979 | Suzuki et al. | |
| 4,259,376 A | 3/1981 | Feldstein | |
| 4,547,157 A | * 10/1985 | Driskell | ........................ 433/173 |
| 4,818,559 A | 4/1989 | Hama et al. | |
| 5,049,074 A | 9/1991 | Otani et al. | |
| 5,110,292 A | 5/1992 | Balfour et al. | |

(Continued)

FOREIGN PATENT DOCUMENTS

| | | |
|---|---|---|
| CH | 444 376 | 3/1965 |
| CH | 444376 | 9/1967 |

(Continued)

OTHER PUBLICATIONS

Hans. H. Brandt, Einführung in die Implantologie, 1996, pp. 38-39, 50-51 and 90-91.

(Continued)

*Primary Examiner* — Yogesh P Patel
(74) *Attorney, Agent, or Firm* — Oliff PLC

(57) ABSTRACT

A dental implant is disclosed comprising an anchoring part for anchoring within a bone and comprising a mounting part for receiving a prosthetic build-up construction, wherein the anchoring part and the mounting part are configured integrally of a material comprising zirconia, wherein at least the anchoring part is treated at its outer surface at least partially by a subtractive, removing process, such as by sand blasting or is provided with a coating which facilitates an ossification.

14 Claims, 2 Drawing Sheets

(56) References Cited

U.S. PATENT DOCUMENTS

| | | | |
|---|---|---|---|
| 5,205,745 A * | 4/1993 | Kamiya | A61C 8/0022 433/173 |
| 5,205,746 A | 4/1993 | Chanavaz | |
| 5,564,923 A | 10/1996 | Grassi et al. | |
| 5,642,996 A * | 7/1997 | Mochida et al. | 433/174 |
| 5,782,918 A * | 7/1998 | Klardie et al. | 606/60 |
| 5,816,809 A * | 10/1998 | Sapkos | A61C 8/005 433/172 |
| 5,934,287 A | 8/1999 | Hayashi et al. | |
| 6,050,819 A | 4/2000 | Robinson | |
| 6,165,925 A * | 12/2000 | Rieger | 501/103 |
| 6,174,167 B1 | 1/2001 | Wuhrle | |
| 6,290,500 B1 * | 9/2001 | Morgan | A61C 8/0048 433/173 |
| 6,375,465 B1 * | 4/2002 | Engman | A61C 8/0022 433/172 |
| 6,402,517 B1 | 6/2002 | Hozumi et al. | |
| 6,527,554 B2 | 3/2003 | Hurson et al. | |
| 6,534,197 B2 | 3/2003 | Noda et al. | |
| 6,655,962 B1 * | 12/2003 | Kennard | 433/174 |
| 2002/0182567 A1 | 12/2002 | Hurson et al. | |
| 2003/0082498 A1 * | 5/2003 | Halldin et al. | 433/173 |
| 2003/0176927 A1 * | 9/2003 | Steinemann et al. | 623/23.55 |

FOREIGN PATENT DOCUMENTS

| | | |
|---|---|---|
| DE | 3233992 A1 | 3/1984 |
| DE | 101 59 683 | 11/2001 |
| DE | 101 59 683 A1 | 6/2003 |
| EP | 0 092 209 | 10/1983 |
| EP | 0 111 134 | 10/1983 |
| EP | 0 111 134 | 6/1984 |
| EP | 0 388 576 | 11/1989 |
| EP | 0 388 576 | 9/1990 |
| GB | 1083769 | 9/1965 |
| GB | 1083769 | 9/1967 |
| JP | 7112000 A | 5/1995 |
| WO | WO 86/03666 | 7/1986 |
| WO | WO 91/03213 | 8/1989 |
| WO | WO9103213 A1 | 3/1991 |
| WO | PCT/WO96/16611 | 11/1995 |
| WO | WO 96/16611 | 6/1996 |
| WO | WO 96/19947 | 7/1996 |
| WO | WO 99/39653 | 8/1999 |
| WO | 00/23003 A1 | 4/2000 |
| WO | WO0121091 A1 | 3/2001 |
| WO | WO 01/34056 A1 | 5/2001 |

OTHER PUBLICATIONS

Spiekermann, Hubertus, Band 10 Implantologie, Schraubenimplantate nach Ledermann, p. 52.
Schroeder, et al., Orale Implantologie, 1994, 199-211.
André Schroeder, Franz Sutter, Daniel Buser and Gisbert Krekeler "Oral Implantology, Basics, ITI Hollow Cylinder System", 1996, Chap. 7, "The Concept of the ITI Implants", pp. 123-132.
ISO 13356 Implants for surgery—Ceramic materials based on yttria-stabilized tetragonal zirconia (Y-TZP), 1997, pp. 1-7.
JP7328036, Dec. 19, 1995, Ushito Toshio, "Intraosseous Implant and Manufacture Thereof".
JP7328038, Dec. 19, 1995, Murata Takeshi; Kaneko Norio; "Intraosseous Implant".
JP11228221, Aug. 24, 1999, Nawa Masahiro; "Zirconia-Based Composite Ceramic Sintered Compact for Biological Use".
JP61146757, Jul. 4, 1986, Ishizawa Kenki; Ayusawa Nobuo; Kuroshima Hiroshi; "Zirconia Implant Member for Artificial Tooth Root".
JP2001269357, Oct. 2, 2001, Noda Iwao; Ikeda Junji; Nakanishi Takefumi; Kitano Hiroyuki; Masuda Shingo, "Living Body Implant Material, and Method of Manufacturing for the Same".
JP2001017447, Jul. 31, 2000, Hozumi Atsushi; Inagaki Masahiko; Nishizawa Kaori; Nagata Fukue; Yokogawa Yoshiyuki; Kameyama Tetsuya, "Artificial Root of Tooth Having Polluting Substance/Bacteria Adhesion Restricting Function and Acid Resistance, and Manufacture Thereof".
Wikipedia, Glass Ceramics, Jun. 1, 2006, Von, http://de.wikipedia.org/wiki/Glaskeramik, with English translation.
Kern et al., First Clinical Experiences with Root Posts Made of Zirconium Oxide Ceramics, Dtsch Zahnarzh Z53, 1998, pp. 266-268, with English translation of abstract.
Seitner et al., Fully Ceramic Restorations of Heavily Destructed Lateral Teeth, Quintessenz 48, 4, 1997, pp. 499-514, with English translation of abstract.
Simon, M.H.P., New Perspectives on Fully Ceramic Stabilization and on Construction of Devital Teeth, Aug. 1995, pp. 1085-1101, with English translation of abstract.
Akagawa et al., "Interface histology of unloaded and early loaded partially stabilized zirconia endosseous implant in initial bone healing," The Journal of Prosthetic Dentistry, 69(6):599-604, (1993).
Buser et al., "Influence of surface characteristics on bone integration of titanium implants. A histomorphometric study in miniature pigs," Journal of Biomedical Materials Research, 25:889-902, (1991).
"Auszug aus Patientenkartei" (Excerpt from the patient database) from Dr. U. Volz, Mar. 2001. (short description enclosed).
Glaskeramik, aus Wikipedia, der freien Enzyklopädie, http://de.wikipedia.orq/wiki/glaskermik, (2006) (and equivalent English language page).
Godfredsen et al., "Anchorage of TiO$_2$-blasted, HA-coated, and machined implants: An experimental study with rabbits," Journal of Biomedical Materials Research, 29:1223-1231, (1995).
Godfredsen et al., "Histomorphometric and removal torque analysis for TiO$_2$-blasted titanium implants," Clin. Oral Impl., 3:77-84, (1992).
Gotfredsen et al., "Anchorage of Titanium Implants with Different Surface Characteristics: An Experimental Study in Rabbits," Clin. Implant Dentistry and Related Research, 2(3):120-128, (2000).
Kern et al., "Erste klinische Erfahrungen mit Wurzelstiften aus Zirkonoxidkeramik," Dtsch Zahnärztl Z 53(4):266-268, (1998), München, Germany.
Martin et al., "Effect of titanium surface roughness of proliferation, differentiation, and protein synthesis of human osteoblast-like cells (MG63)," Journal of Biomedical Materials Research, 29:389-401, (1995).
Medical Masters AG, Meersburg, Germany, (2005): Letter to Z-Systems GmbH & Co., KG (short description enclosed).
Metoxit, High Tech Ceramics, Technical Report, pp. 1-4, (Jan. 13, 2005). (short description enclosed).
Seitner et al., "Vollkeramische Restautationen bei stark zerstörten Seitenzähnen," Quintessenz, 48(4):499-514, (1997).
Simon et al., "Neue Perspektiven zur vollkeramischen Stabilisierung und zum Aufbau devitaler Zähne," Quintessenz, 46:1085-1101, (1995).
Invitation and list of attendees, 6th Therapeutentreffen, Meersburg, Germany, (2001). (2 pages) (short description enclosed).
Presentation slides from Dr. Volz,, "Zirkon-Wunderwerkstoff der Zukunft?", Bodensee Zahnklinik AG, Meersburg, Germany, (2001) (64 pages). (short description enclosed).
Wennerberg et al., "Design and Surface Characteristics of 13 Commercially Available Oral Implant Systems," The International Journal of Oral & Maxillofacial Implants, 8(6):622-633, (1993).
Wennerberg et al., "Experimental study of turned and grit-blasted screw-shaped implants with special emphasis on effects of blasting material and surface topography," Biomaterials, 17(1):15-22, (1996).
Specifications for DIN EN ISO 4287 and DIN EN ISO 4288 Standards.
Interface histology 1993. pp. 599-604 attached.
Buser D, Journal of Biomedical Materials Research, vol. 25, 889-902 (1991).
Gotfredsen 1992, pp. 77-84 attached.
Gotfredsen 1995, pp. 1223-1231 attached.
Gotfredsen 2000, pp. 120-128 attached.
Martin 1995, pp. 389-401 attached.
Wennerberg 1996, Biomaterials, vol. 17, pp. 15-22, attached.
Wennerberg 1993, International Journal of Oral & Maxillefacial Implants, pp. 622-633.

(56) References Cited

OTHER PUBLICATIONS

Auszug wikipedia.
DIN EN ISO 4288.
DIN EN ISO 4287.
Interface histology 1993.
Buser D.
Gotfredsen 1992.
Gotfredsen 1995.
Gotfredsen 2000.
Martin 1995.
Wênnerberg 1996.
Wennerberg 1993.
Feb. 1, 2018 Office Action issued in U.S. Appl. No. 14/978,781.
May 19, 2017 Office Action issued in U.S. Appl. No. 14/978,781.
Vortragsunterlagen.
Therapeutentreffen.
Medical Masters.
Dr. Volz Auszug Patientenkartel.
Die Oulntessenz 8.
Oulntessenz 48.

* cited by examiner

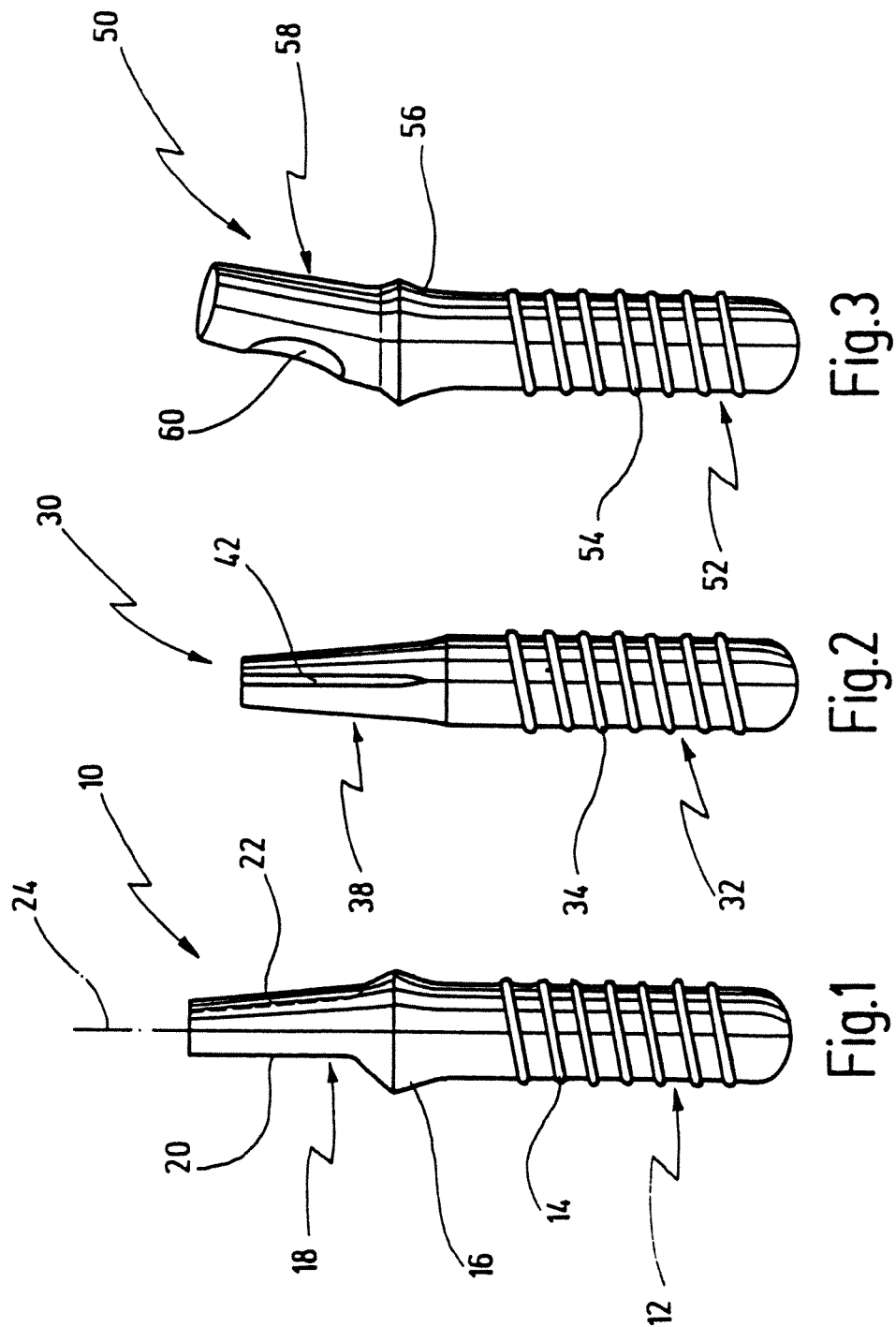

CERAMIC DENTAL IMPLANT

RELATED APPLICATIONS

This application is a divisional application of U.S. patent application Ser. No. 10/496,814, filed on Dec. 17, 2004, which is a continuation application of copending international patent application PCT/EP02/13187 filed on Nov. 23, 2002 claiming priority of German patent application 101 59 683.9, the disclosures of all of which are hereby incorporated by reference.

BACKGROUND OF THE INVENTION

The invention relates to a dental implant comprising an anchoring part for anchoring within the bone and comprising a mounting part for receiving an element to be attached, such as an abutment or a crown, a bridge or a prosthesis construction.

Dental implants have been successfully used since more than 10 years. The major part of the dental implants currently used consist of titanium, since titanium has a sufficiently low elastic modulus and also has a relatively large strength. In addition, it is of particular importance that when using titanium as an implant material a safe integrating or interlocking osteogenesis can be reached when the surface is suitably treated (e.g. roughened by sand blasting). This means that the titanium implants, after reaching a primary stability by screwing into the bone, safely ossify within a healing time of about 3 to 4 months so that a permanent bond between the anchoring part screwed into the bone and the bone is guaranteed. Herein usually two-part implants are utilized. Basically, there are two possibilities for this end:

According to a closed sub gingival system the anchoring part of the implant is embedded until the bone ridge so that the mucoperiost cover can be sewn above the implant. Herein a drawback is the necessary secondary operation at the end of the primary healing phase for allowing a subsequent application of a mounting part, and thereon the desired prosthesis or crown.

By contrast, when using the open transgingival system, then the anchoring part of the implant can be sunk in up to about 3 mm above the bone ridge at mucosal level, thus avoiding a secondary operation. The wound edges can be directly adapted to the implant neck portion, thereby effecting a primary soft tissue closure to the implant.

Such a two-part implant construction for an open transgingival system is e.g. marketed by Institut-Straumann AG, Waldenburg/Switzerland under the mark ITI®DENTAL IMPLANT SYSTEM. Both the anchoring or primary part which is implanted transgingivally, as well as the assigned construction parts herein consist of pure titanium. To guarantee a good ossification the titanium surface is either coarsely sand blasted or is coated with titanium by thermal spraying. Both surfaces guarantee a good ossification or interlocking osteogenesis.

Thereafter onto the mounting part of such implants prosthesis elements, such as bridges or crowns, are usually screwed or cemented usually using intermediate so called abutments. Lately to this end also ceramic abutments have been developed that are applied onto the mounting part.

Ceramic abutments offer particular advantages during the subsequent matching of the supra-construction, such as bridges or crowns, to the abutment. They can be simply ground and allow to build constructions using prior art processes known to the dentist. Ceramic abutments offer particular advantages due to the fact that their color can be closely matched to the natural tooth color. Lately also abutments of zirconia have been developed which offer a particularly high strength.

Such a system consisting of two-part implants having an anchoring part and a mounting part, an abutment and a prosthesis applied thereon offers a good matching to the geometric situation for different indications, however, generally the multitude of the components used. is detrimental for the mechanical stability of the total system. Also each further bonding leads to possible starting points for bacteria which may cause parodontitis or gingivitis within the gap.

However, from an aesthetic point of view in particular in the front visible region it would be desired to make all transgingival parts, also the anchoring part, of ceramic. However, a screw connection between metal (anchoring part of titanium) and ceramic (mounting part) cannot be realized, inter alia, due to the differences in the coefficients of thermal expansion. By contrast, up to now anchoring parts made of ceramic could not pervade, since these usually do not have the necessary mechanical stability or do not provide safe ossification.

Lately also zirconia.ceramics have become available that have an extremely high strength, in particular when the shaped bodies are prepared by hot isostatic pressing or by sintering followed by hot isostatic densifying. Such a zirconia ceramic which may comprise roughly 92.1-93.5 wt.-% $ZrO_2$, 4.5-5.5 wt.-% $Y_2O_3$ and 3.8-2.2 wt.-% $HfO_2$, is for instance known from U.S. Pat. No. 6,165,925.

However, the application of zirconia ceramic as a material for making the anchoring part of an implant seems not possible, since a sufficient mechanical stability of the zirconia ceramic is necessary, this requiring a highly dense preparation, practically without any porosity to be measured, this simultaneously leading to a clean cut extremely hard surface.

Such a material is bio-inert, so that no interlocking osteogenesis is to be expected, this is why this material is not regarded to be suitable for the preparation of an anchoring part of an implant.

From DE 195 30 981 A1 a pre-manufactured fully ceramic implant supra-construction of zirconia is known for the design of artificial crown frustums of tooth color attached to implants. Although herein some kind of advantages with respect to the aesthetic of zirconia ceramic and possibly with respect to a simplified preparation for the design of the supraconstruction is made possible, however also this implant construction bears the basic disadvantages that rest with multiple-part implant constructions. Namely, since the implant itself consists of titanium, the same problems as before result within the bonding region between the implant and the supraconstruction made of zirconia ceramic.

Further reference is made to DE 40 12 731 A1 which discloses several processes for the treatment of implants to generate a defined coarse surface. However, the known system still suffers from the drawbacks inherent with metal implants.

Finally, reference is made to DE 28 38 759 A1 which discloses an implant consisting of a metal, a plastic or a ceramic that is covered with a layer system consisting of a passivating layer and/or of several physiologically active layers. Herein in particular a passivating layer of silicon nitride and a physiologically active layer of calcium fluoride, of carbon or the like is contemplated. However, also this implant does not guarantee a safe ossification within the bone after implantation.

SUMMARY OF THE INVENTION

Thus, it is a first object of the invention to disclose an improved dental implant which provides a high mechanical stability for the total system.

It is a second object of the invention to disclose a dental implant which is made of ceramic.

It is a third object of the invention to disclose a dental implant having a color that is approximated to the color of a human tooth.

It is a forth object of the invention to disclose a dental implant that offers a safe ossification within a short healing time after implantation into the human mouth.

It is a fifth object of the invention to disclose a process of making such an implant.

It is a sixth object of the invention to disclose a one-part ceramic implant comprising an anchoring part for anchoring within a human bone and a mounting part integral with the anchoring part and being adapted for attaching dental elements thereto.

According to the invention, these and other objects are achieved by a dental implant comprising an anchoring part for anchoring within the bone, and comprising a mounting part for receiving an element to be applied, wherein the anchoring part and the mounting part are integrally made of a material based on zirconia, and wherein at least the anchoring part is treated at its outer surface by a subtractive removing process, or is provided with a coating, whereby an ossification is facilitated.

The material may be pure zirconia or, preferably, may be stabilized zirconia that comprises at least 90 vol.-% of pure zirconia.

In addition, this object is achieved by a process for making a dental implant, wherein initially a base body having an anchoring part for anchoring within the bone and a mounting part for receiving an element to be applied, is provided integrally from a material based on zirconia, and wherein subsequently at least the anchoring part is treated at its outer surface at least partially by a subtractive, removing process or is coated with a coating that facilitates ossification.

The object of the invention is completely achieved in this way.

Surprisingly it has been found that in this way a one-part dental implant having an anchoring part and a mounting part can be prepared that consists of a material comprising zirconia and which still guarantees a good ossification during a short healing time.

Herein a particular advantage must be seen in the one-part design of the implant that in combination with a high strength of zirconia ceramic guarantees a high stability of the total system. Simultaneously there is the particular advantage that the mounting part can be approximated to the natural tooth color and thus in particular in the visible region allows the preparation of completely natural looking ceramic reconstructions. In addition, the mounting part can be directly ground which allows a simple and advantageous adaptation of the additional elements to be applied. Possibly additional abutments may become superfluous.

Preferably, the implant according to the invention is applied transgingivally. Thus the soft tissue attachment developing the biological breadth is not disturbed by a secondary operation such as occurring with systems that heal with overed mucous linings.

According to the invention after the implantation a primary treatment by applying a temporary part directly onto the mounting part is made possible. To this end after reaching a sufficient primary stability, e.g. by screwing the anchoring part into a bone bore, only measures must be taken to avoid in particular shearing motions during the subsequent healing time. In case of several implants this can be effected by a blocking, while with single implants this can be effected by an attachment to adjacent teeth or to prosthetic parts partially by applying adhesive.

Preferably the anchoring part comprises a threaded section.

Thereby the implant according to the invention can be implanted with the necessary primary stability so that subsequently to the implantation directly a primary treatment is made possible by applying a temporary part.

According to a further embodiment of the invention the anchoring part at its outer surface is at least partially roughened by a removing process or is micro-structured.

Such a surface structuring guarantees that the zirconium oxide material which would otherwise be bio-inert can reach an integral osteogenesis with the bone material.

For reaching a good interlocking osteogenesis it is preferred in this regard, when the dental implant in the region of the anchoring part has a maximum surface roughness between 1 and 20 µm, preferably between 2 and 15 µm, in particular between 4 and 12 µm, particularly preferred between 6 and 12 µm.

Basically to this end an abrasive blasting, such as sand blasting (using corundum), a blasting with boron carbide particles, or a high-pressure water blasting, is possible. However, problematic with such a treatment is the high hardness of the zirconium oxide ceramic. Therefore, a considerably improved surface roughness can be reached by using a hard material for blasting, such as boron carbide particles which is considerably costly, however.

Therefore, alternatively also chemical processes, such as etching processes, are contemplated which partially may be applied as a subsequent treatment in addition to a previous mechanical treatment.

Apart from that also for such removing processes laser-based processes are contemplated.

In particular preferred is to perform an initial blasting treatment, such as sand blasting with $Al_2O_3$, and a subsequent etching treatment using phosphoric acid, sulphuric acid, hydrochloric acid or mixtures thereof.

Herein the blasting treatment may be performed using a pressure between about 1 bar and 10 bars, preferably between 2 and 6 bars, in particular between 3 and 5 bars.

Herein in particular, as a subsequent treatment after a blasting treatment, an etching treatment is desired using phosphoric acid of 10 to 90 vol.-%, preferably of 15 to 50 vol.-%, in particular of 20 to 40 vol.-%.

The etching may e.g. be performed for a time of 10 seconds to 10 minutes, preferably between 10 and 120 seconds, in particular between about 15 to 60 seconds.

The etching treatment suitably is followed by a cleaning step, such as rinsing within a NaCl solution and subsequent rinsing in deionized water.

According to a further embodiment of the invention the anchoring part at its outer surface is at least partially provided with a bio-active coating.

This may for instance be a silanization or a hydroxylation which also facilitates osteogenesis.

According to a further embodiment of the invention the anchoring part is at least partially coated with a metallic or ceramic coating or with a cermet coating. Herein the anchoring part may e.g. be coated by thermal spraying, by CVD or by PVD.

In particular, a coating consisting of titanium or of a titanium alloy is regarded as advantageous, which possibly may be applied by thermal spraying.

With such a coating the bio-compatibility of titanium having been known since years, can be utilized for reaching a safe interlocking osteogenesis of the anchoring part during the healing phase. The titanium possibly applied by thermal spraying has a sufficient micro-structuring to avoid a distant osteogenesis and to guarantee a safe ossification.

Preferably, herein only the surface of the anchoring part is coated that will be recessed within the bone during implantation. Thereby the advantageous aesthetics of the zirconia-based ceramic in the region of the mounting part can be combined with the advantageous bio-compatibility of titanium.

Suitably the mounting part comprises a support for applying a screwing tool.

Herein the mounting part may be designed for positive fitting of a screwing tool, such as basically already known in the art.

In general, the dental implant can be designed with all kinds of implant shapes already known or to be developed.

Herein the mounting part may be configured as an extension of the anchoring part or may be offset with respect to the anchoring part.

Also the mounting part may have a frusto-conical basic shape, this facilitating an adhesive attachment of abutments for prosthesis constructions.

Naturally, in addition also further shapes of the mounting part are possible, such as a square shape or a hexagonal shape.

According to a further embodiment of the invention the dental implant is stored in a suitable liquid, such as deionized water, after a previous activation of its surface, such as by silanization or hydroxylation or by an etching treatment, before it is implanted by the doctor. Thus the dental implant may be stored within a container, preferably without air access.

Thereby it is avoided that the surface of the dental implant before mounting loses its activation fully or partially due to air constituents. In this wayan ossification is facilitated.

The generation of a zirconia ceramic for the dental implant is basically known in the art and is not regarded as being part of the invention. In this regard it is referred e.g. to U.S. Pat. No. 6,165,925 mentioned at the outset, which is fully incorporated by reference. A zirconia ceramic prepared in this way may for instance be processed by grinding to the desired shape of the implant. According to the invention it is then surface-treated to reach the desired surface characteristics.

It will be understood that the above-mentioned and following features of the invention are not limited to the given combinations, but are applicable in other combinations or taken alone without departing from the scope of the invention.

BRIEF DESCRIPTION OF THE DRAWINGS

Further features and advantages of the invention will become apparent from the following description of preferred embodiments taken in conjunction with the drawings. In the drawings show:

FIG. 1 a side view of a first embodiment of an implant according to the invention;

FIG. 2 a side view of an embodiment of an implant according to the invention slightly modified with respect to the embodiment of FIG. 1;

FIG. 3 a side view of a further embodiment of an implant according to the invention wherein the mounting part is slightly offset with respect to the anchoring part;

DETAILED DESCRIPTION OF THE PREFERRED EMBODIMENTS

Figure 4:
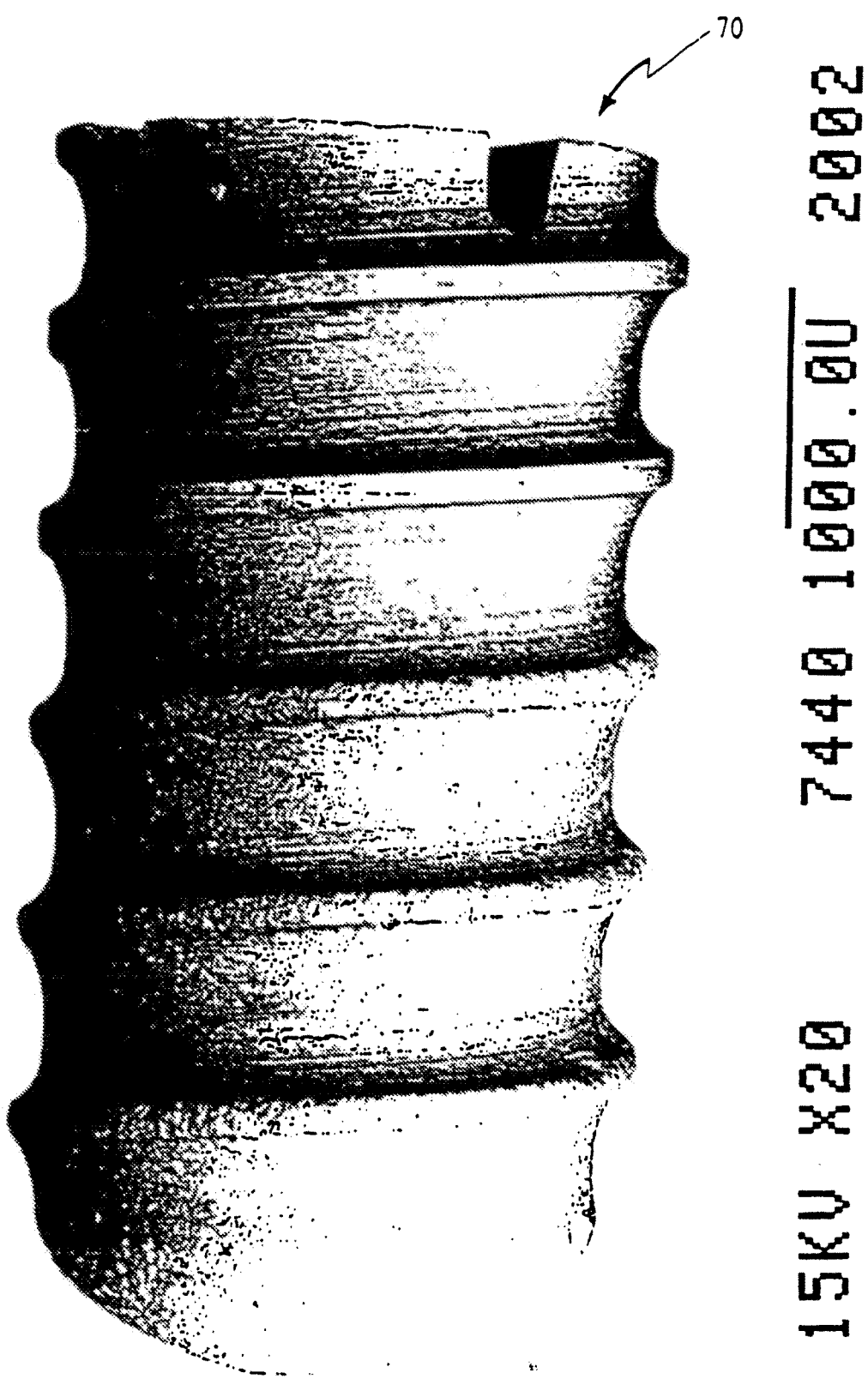
FIG. 4 a SEM photograph of a test specimen of an implant which has been implanted into a patient and which has been removed together with the adjacent bone material using a drill after a healing period of about 3 months.

In FIGS. 1-3 several possible embodiments of a one-part dental implant according to the invention are depicted, this being purely exemplary without limiting the scope of the invention to any kind of shape of the implant.

In FIG. 1 a dental implant according to the invention is designated in total with numeral 10. It comprises an anchoring part 12 having a threaded section 14 and a rounded lower end . The anchoring part 12 at its upper end transitions via a slightly enlarged conical section 16 to the outside into a mounting part 18 being integral therewith and extending within an extension of the longitudinal axis 24 of the threaded section 14. The mounting part 18 has a frusto-conical or a conical shape and is provided with a flattening 20 at one side thereof. At the side opposite the flattening 20 there is provided a groove 22 within the outer surface that extends from the upper front surface of the mounting part 18 toward the lower side and ends in a conical section which forms the transition to the conical section 16 of the anchoring part 12.

The flattening 20 in combination with the groove 22 located on the opposite side functions to provide a positive a screwing tool which has a plug-in seat matched thereto.

FIG. 2 shows a slightly modified embodiment of a dental implant designated in total with numeral 30 which again comprises an anchoring part 32 having a threaded section 34 being followed by a conical mounting part 38 on which the groove 42 can be seen, since the dental implant 30 is depicted rotated by 90° with respect to the dental implant 10 of FIG. 1.

By contrast to the embodiment shown in FIG. 1 the dental implant 30 does not have a conical section within the transitional region between the anchoring part 32 and the mounting part 38. Instead, the mounting part 38 is configured as a conical section directly adjoining the anchoring part 32 which is shaped cylindrically. Again on the side opposite to the groove 42 a respective flattening may be provided, such as can be seen in FIG. 1.

In FIG. 3 a modified embodiment of the dental implant is designated in total with numeral 50.

The dental implant 50 comprises an anchoring part 52 corresponding to the embodiment according to FIG. 1 and having a threaded section 54 which transitions via an outer conical section 56 into a mounting part 58.

Again the mounting part 58 has a conical basic shape, however, is offset with respect to the longitudinal axis of the anchoring part 52, e.g. by an angle of about 15°, this being particularly suitable for applications within the incisor region in many cases. Again, by a suitable recess 60 at the outer surface of the mounting part 58 a positive engagement of a screwing tool is made possible to also allow to screw into a bone bore this dental implant having an offset mounting part.

The anchoring part may e.g. have an axial length of 10 mm, wherein the other dimensions result in a corresponding manner. However, it should be understood that the dimensions and the shape may be modified in a suitable way, depending on the respective indication.

The dental implants 10, 30, 50 according to the invention are prepared integrally from a zirconia ceramic which e.g. may be a stabilized zirconia ceramic having 92.1 to 93.5 wt.-% $ZrO_2$ and 4.5 to 5.5 wt.-% $Y_2O_3$ and 1.8 to 2.2 wt.-% $HfO_2$ according to U.S. Pat. No. 6,165,925 mentioned at the outset. Such a stabilized zirconia ceramic, in particular, when prepared by hot isostatic pressing or by sintering with subsequent hot isostatic densification offers a particularly high mechanical stability and strength. Also the utilization of any other zirconia ceramics is conceivable.

The anchoring part at its outer surface thereof has been treated by a suitable removing pretreatment or by a suitable coating to thereby reach a good interlocking osteogenesis after implantation. E.g. the anchoring part may be silanated or hydroxylated or may be roughened by a removing process or may be micro-structured.

Also using a coating which is preferably applied by thermal spraying with a layer thickness preferably being in the range between about 20 and 100 µm, an interlocking osteogenesis can be reached.

Apart from ceramic coatings e.g. consisting of zirconia, alumina, silica or mixtures thereof with possible further constituents, in particular a coating by thermal spraying is preferred consisting of pure titanium having a layer thickness of about 20 to 100 µm.

It is suggested to perform a suitable pretreatment of the surface before the spraying the coating possibly by plasma spraying, to guarantee a sufficient roughness for a good adhesion of the coating, e.g. using abrasive blasting or an etching treatment.

Using a thin, thermally sprayed coating, in particular consisting of titanium applied only in the region of the anchoring part (not in the visible region), a safe integral osteogenesis can be reached during healing time, wherein simultaneously the advantages of zirconia ceramic, such as grinding possibility and a color approximated to the natural tooth can be utilized.

By means of first field tests it has been shown that a one-part zirconia implant, the outer surface of which has merely been subjected to a subtractive treatment, can guarantee an integrating osteogenesis.

EXAMPLE

Test implant specimen according to FIG. 4 were prepared from a zirconia ceramic according to U.S. Pat. No. 6,165,925 and were processed by grinding to yield the shape according to FIG. 4.

Thereafter, the surface of the specimen was sand blasted with corundum using a blasting pressure of 4 bars. This yielded a maximum surface roughness of 6.4 µm with an average surface roughness of about 4.7 µm.

The test implant sample 70 shown in FIG. 4 was implanted into a patient. After a healing time of about 3 months the test implant sample was removed together with a small amount of the surrounding bone material using a hollow drill and was analyzed histologically with respect to osteointegration. It was found that an integrating osteogenesis can be reached.

Additional improvements with respect to an integrating osteogenesis already after short healing time are particularly expected when using increased surface roughness in the range of about 5 to 15 µm $R_{max}$ which may be reached solely by sand blasting. Also a subsequent treatment of the blasted surface by etching with phosphoric acid is contemplated. In particular, by etching with phosphoric acid of 30% for a time of 30 seconds, using a subsequent rinsing initially with NaCl solution and thereafter with deionized water, the surface roughness can be increased to 5 to 15 µm $R_{max}$ (in particular to about 8 to 12 µm, depending on the previous blasting treatment)

In addition, the activation of the surface reached by etching facilitates an integrating osteogenesis. To keep this activation until implantation, in addition it is preferred to store the implant directly after the etching and rinsing treatment in a suitable liquid, such as deionized water, until the implant is implanted by the doctor. In this way it is avoided that the surface loses its activation fully or partially by means of air constituents, before the dental implant is applied.

The invention claimed is:

1. A one-part dental implant comprising:
an anchoring part for anchoring within bone and having a threaded section with a longitudinal axis; and
a mounting part having a frustoconical or conical shape and lying in an extension of the longitudinal axis of the threaded section of the anchoring part, the mounting part including a flattened portion that has a smaller outer diameter than a remainder of the one-part dental implant, wherein:
the mounting part is configured to receive an element selected from the group consisting of a crown, a bridge, and a prosthesis;
an upper end of the anchoring part transitions via an enlarged conical section into the mounting part, the enlarged conical section having a larger outer diameter than a remainder of the one-part dental implant;
the anchoring part and the mounting part are integrally made of a material based on zirconia;
the anchoring part at its outer surface is at least partially roughened; and
the one-part dental implant facilitates osteogensis with the bone.

2. The dental implant of claim 1, wherein the mounting part has a groove at the side opposite the flattened portion.

3. The dental implant of claim 2, wherein the groove extends from an upper front surface of the mounting part toward a lower side and ends at the enlarged conical section.

4. The dental implant of claim 1, wherein the anchoring part has an abrasively blasted outer surface.

5. The dental implant of claim 1, wherein the anchoring part has a sand blasted outer surface.

6. The dental implant of claim 1, wherein the anchoring part has an etched outer surface.

7. The dental implant of claim 1, wherein the anchoring part has an abrasively blasted and subsequently etched outer surface.

8. The dental implant of claim 6, wherein the anchoring part has a surface etched with an etchant comprising at least one component selected from the group consisting, of phosphoric acid, sulphuric acid, hydrochloric acid, and mixtures thereof.

9. The dental implant of claim 6, wherein the anchoring part has a surface etched with phosphoric acid of 10 to 50 vol. %.

10. The dental implant of claim 1, wherein an outer surface of the anchoring section is silanated.

11. The dental implant of claim 1, wherein an outer surface of the anchoring section is hydroxylated.

12. The dental implant of claim 1, wherein the anchoring part and the mounting part are integrally made of 92.1 to 93.5% by weight $ZrO_2$, 4.5 to 5.5% by weight $Y_2O_3$, and 1.8 to 2.2% by weight $HfO_2$.

13. The dental implant of claim 1, wherein at least the threaded section of the anchoring section has a maximum surface roughness between 4 and 20 micrometers.

14. The dental implant of claim 1, wherein at least the threaded section of the anchoring section has a maximum surface roughness between 4 and 12 micrometers.

\* \* \* \* \*